United States Patent [19]

Taylor

[11] 4,010,078
[45] Mar. 1, 1977

[54] DEVICE FOR USE IN THE IDENTIFICATION OF MICROORGANISMS

[76] Inventor: Welton I. Taylor, 7621 S. Prairie, Chicago, Ill. 60619

[22] Filed: Feb. 23, 1976

[21] Appl. No.: 660,480

[52] U.S. Cl. .................. 195/139; 195/103.5 R; 195/103.5 M
[51] Int. Cl.² .................................... C12K 1/10
[58] Field of Search ................................... 195/139

[56] References Cited
UNITED STATES PATENTS

| | | | |
|---|---|---|---|
| 3,179,574 | 4/1965 | Harrison | 195/139 |
| 3,597,326 | 8/1971 | Liner | 195/139 |
| 3,632,478 | 1/1972 | Fink | 195/139 |

*Primary Examiner*—Raymond N. Jones
*Assistant Examiner*—Robert J. Warden
*Attorney, Agent, or Firm*—Wallenstein, Spangenberg, Hattis & Strampel

[57] ABSTRACT

A device for use in the identification of microorganisms comprising, in a preferred form, an open-topped, multi-compartmented microorganism culture media receiving portion and a cover member. Each compartment, or well, of the culture media receiving portion is adapted to receive a solid medium. The number of wells provided, and the type of media employed, enable a wide variety of microorganisms to be identified accurately in the shortest possible time in a single, compact unit. The device can be used with equal facility for the identification of both aerobic and anaerobic microorganisms.

8 Claims, 3 Drawing Figures

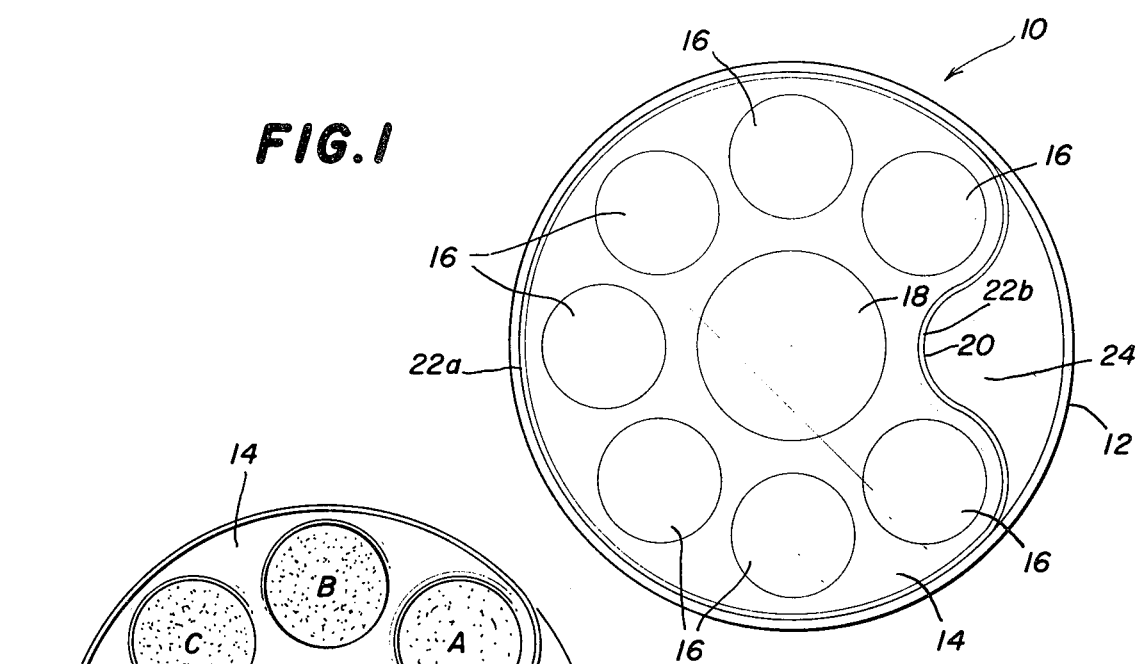
FIG.1
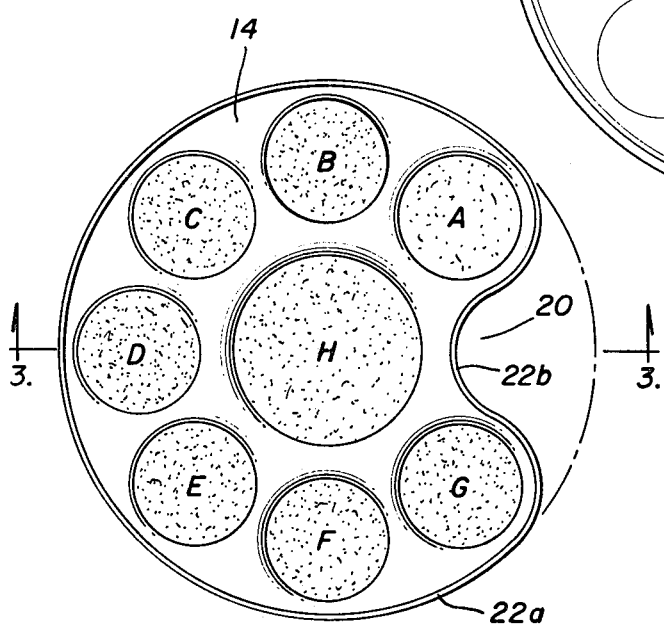
FIG.2
FIG.3
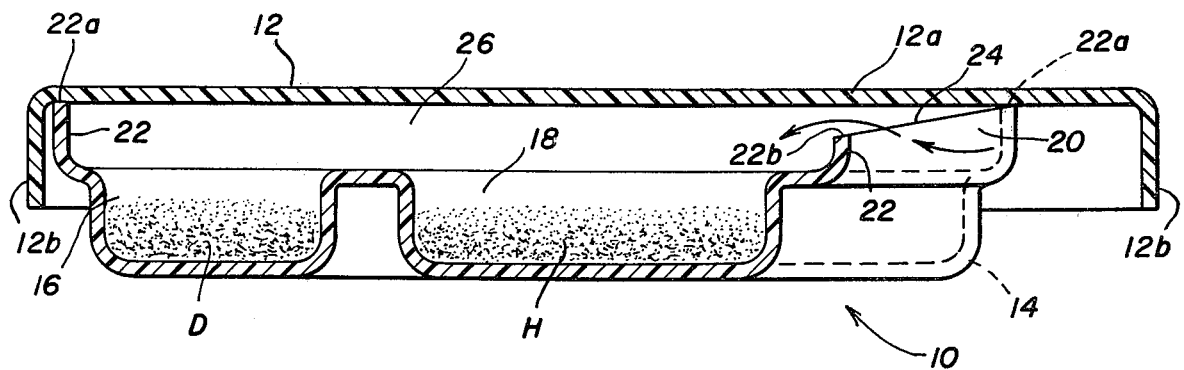

DEVICE FOR USE IN THE IDENTIFICATION OF MICROORGANISMS

The present invention relates to a device for use in the identification of microorganisms having clinical importance as well as microorganisms having importance in the food, drug, cosmetics and textile industries.

The need for a device which will enable accurate, yet rapid, identification of microorganisms, particularly those having clinical significance, has long been recognized by physicians and microbiologists. This need is especially apparent in those cases where pathogenic non-fermentative Gram negative rods, other than pathogens of the family Enterobacteriaceae, are involved. The difficulties encountered in the identification of non-fermenting rods center around anomalies in the growth characteristics of these microorganisms. Thus, for example, non-fermentative Gram negative rods require heavy inocula and generally longer incubation times to stimulate growth. Also, they are strict aerobes, and will not, as a result, grow in agar deeps or broth tubes except on the surface. In addition, they will not show oxidation of sugars in media used in the identification of enterics. Furthermore, pigment may be produced by non-fermenters only on certain media, or after several days incubation, or only at room temperature. The observance of the motility of non-fermenters also is a problem since they will not grow in conventional tubed motility media.

Still another family of microorganisms which present special identification problems are the yeast pathogens. The growth patterns of these microorganisms are such that their accurate identification in many instances requires the services of a professional clinical mycologist. The relatively small number of trained mycologists available for this purpose has emphasized the need for a device which will enable laboratory technicians or para-professionals not only to make accurate identifications of yeast pathogens, but, also, to do so within a time period which will enable a physician to prescribe treatment which will most effectively, efficiently and expeditiously meet a patient's requirements. So far as is known, no device heretofore has been developed which satisfies these desiderata.

In accordance with the present invention, a device has been evolved which enables accurate identification of non-fermentative Gram negative rods as well as yeast pathogens to be made in an optimum time period without requiring the services of a highly skilled professional. The device is adapted to receive solid culture media which favor the growth of these pathogens. The number of media incorporated in the device and the nature thereof are preselected to enable a user to identify substantially all of the clinically significant non-fermenters and yeast pathogens. The device is provided with means for establishing an atmosphere which favors the growth of the microorganisms introduced into the culture media while at the same time shielding the media from air-borne, or other, contaminants. The device, in addition, is provided with integral indexing means for easy orientation of the different media contained in the device. The device is compact in size, and is advantageously fabricated of lightweight, transparent material to facilitate manipulation and to permit ready observance of microorganism generated activity in the culture media.

The device, in brief, comprises a microorganism culture medium receiving portion, and a cover having a top and a depending side wall. In a preferred embodiment of the device, the culture medium receiving portion is formed with eight culture medium receiving compartments or wells each of which is adapted to receive a different culture medium. The culture medium receiving portion has an indention which serves as an effective means for properly orienting the media in the wells. Joined to the outer margin of the culture medium receiving portion is an upwardly extending cover engaging wall, the outer edge of which engages the top of the cover and maintains its spaced relation to the upper surface of the media in the culture medium receiving portion. The cover engaging wall, at the indention formed in the culture medium receiving portion, tapers inwardly so that the upper edge thereof lies in a plane below the horizontal plane of the upper edge of the remainder of the cover engaging wall. This arrangement, in cooperation with the top of the cover, provides a covered air passageway in communication with an air space formed over the culture media in the culture medium receiving portion when the cover is in position thereon. The cover-shielded passageway enables the selective establishment of an atmosphere over the culture media which favors the growth of microorganisms under investigation while preventing contaminants, air-borne, or otherwise, from coming into contact with the culture media. Apart from its unique utility as a means for identifying non-fermentative Gram negative rods and yeast pathogens, the device of the present invention also can be used to advantage, for example, for the identification of other pathogens, particularly, the Enterobacteriaceae, as well as other pathogens, including anaerobic pathogens.

In accordance with a preferred embodiment of the invention, the media is pre-poured in the wells of the device, and the device is packaged in a sealed, sterile wrapper or envelope for shipment to, and ready use by, laboratory personnel.

The foregoing, and other features and advantages of the invention will become apparent from the following description when taken in conjunction with the accompanying drawing wherein:

FIG. 1 is a top plan view of an embodiment of the device of this invention;

FIG. 2 is a top plan view of the culture medium receiving portion of the embodiment of the device illustrated in FIG. 1 showing culture media therein; and FIG. 3 is an enlarged sectional view taken substantially along line 3—3 of FIG. 2 with the cover on.

Referring, now, in greater detail to the drawing, the illustrated embodiment of the device, designated generally by reference numeral 10, comprises a cover 12 and a microorganism culture medium receiving portion 14. The cover 12 and the portion 14 may be fabricated from glass, plastic or even a lightweight metal such as aluminum. From a practical standpoint, however, the device desirably is made of a transparent plastic material such as polyethylene, polypropylene, polystyrene, or the like. The use of such materials lowers the cost of manufacturing the device, and makes disposability after use economically feasible.

The cover 12, as shown, is circular in configuration, and has a flat top 12a to the periphery of which is joined a depending side wall 12b (see FIG. 3).

The culture medium receiving portion 14 of the device 10 also is generally circular in configuration, but has a diameter which is slightly less than that of the top 12a of the cover 12. The portion 14, in the embodiment of the device illustrated, is formed as an integral, one-piece unit having seven separate culture medium receiving compartments, or wells 16, of substantially the same diameter and depth, concentrally arranged about a larger, separate, centrally positioned culture medium receiving compartment, or well 18, having essentially the same depth as the wells 16. The medium receiving portion 14, as shown, advantageously is formed with an inwardly extending, broadly curved indention 20 which imparts to the culture medium receiving portion 14 a distinctive appearance suggestive of that of an artist's pallette. The purpose of the indention 20 will become clear as the description proceeds.

The culture medium receiving portion 14 is further provided with a peripheral, upwardly extending side wall 22 which girds the wells 16. The outer edge 22a of the side wall 22 is adapted to engage the inner surface of the top 12a of the cover 12 and serves to maintain the top 12a in spaced apart relation to the wells 16 and 18 formed in the culture medium receiving portion 14. As best seen in FIG. 3 of the drawing, the side wall 22, at the indention 20, gradually decreases in height, reaching its lowest level of upward extension at the innermost extremity of the indention 20. Thus, the outer edge 22b of the side wall 22, at the indention 20, lies in a plane below the horizontal plane of the edge 22a of the side wall 22. This arrangement provides a covered air-passageway 24 in communication with the space 26 formed above the wells 16 and 18 when the cover 12 is in position on the culture medium receiving portion 14. The passageway 24 enables air to pass, as indicated by the arrows, into the space 26 thereby providing an atmosphere within the device which favors the growth of microorganisms such as non-fermentative Gram negative rods and yeast pathogens, as well as pathogens belonging to the family Enterobacteriaceae. The passageway 24 also can serve as a means through which air can be evacuated from the space 26 in those instances where the device is used for the identification of anaerobic microorganisms. In either case, the top 12a of the cover 12 acts as a shield to prevent contaminants, air-borne, or otherwise, from settling on the surface of the growth media in the portion 14.

While the device 10 can be supplied to a user in the form shown in FIG. 1 of the drawing, that is, without the culture media in the wells, it is, as stated, preferred to supply the device for use with the culture media pre-poured in the wells. Thus, as illustrated in FIG. 2 of the drawing, each of the wells contains a different culture medium designated by the letters A, B, C, D, E, F, G and H. As indicated, the device, with the culture media therein, can be conveniently packaged in a sterile wrapper, or sealed plastic envelope, not shown, for shipment to, and ready use by, laboratory personnel. Indicia may be applied to the base of the wells or adjacent to the open end thereof to enable a user to identify the medium in each of the wells. Since the device will be supplied with the media in the wells always in the same order, or sequence, the indention 20 provides a convenient means for orienting the device so that the user can quickly recognize on which media microorganism activity has occurred, and, thereby, facilitate identification of the microorganism.

In utilizing the device to identify non-fermentative Gram negative rods, the media A, B, C, D, E, F and G in the wells 16 comprise Seller's medium (a commercially available agar medium containing $KNO_3$, $NaNO_2$, mannitol and an indicator, in particular, bromthymol blue), xylose, glucose, lactose, esculin agar, cetrimide agar and SS agar, respectively. The medium H comprises Mueller-Hinton medium.

Identification of a non-fermenter with the device can be achieved as follows: From an isolation plate, pick a single colony of the organism to sensitivity broth with a straight needle, and incubate for use in Kirby-Bauer method and for use in subsequent tests. The remainder the colony on the isolation plate is transferred to a piece of filter paper or white paper towel with an applicator stick. A drop of oxidase reagent is placed on the paper and the reaction noted. When the sensitivity broth is of the correct turbidity for use in the Kirby-Bauer method, the sensitivities are determined and the broth is returned to the incubator. When the broth in the incubator has become moderately turbid, a sterile swab is inserted into the broth. The swab is then used to inoculate the media A through H in the wells 16 and 18 of the device. An antibiotic disc is set in the well H as for sensitivity testing by the Kirby-Bauer method. Following inoculation with the swab, a straight needle is inserted into the broth, and is then stabbed diagonally across and down the medium A. The cover thereafter is positioned on the medium receiving portion of the device, and the device is incubated overnight. A loopful of inoculum from the sensitivity broth is applied to two microslides. A wet mount for observing motility is made by coverslipping one of the slides. A Gram stain is made from the other microslide, and the morphology of the inoculum observed.

The oxidase, motility and Gram stain tests will indicate whether the organism is oxidase positive or negative, motile or non-motile, and whether it has a rod, coccobacillary or diplococcus morphology. Following incubation of the device overnight, the media in the wells 16 and 18 are examined.

A change in medium A to a deep color indicates reduction of nitrate to nitrite. Gas bubble formation in the medium A indicates production of nitrogen gas.

A yellow color in the media B, C and D indicates oxidation.

A brown-black discoloration of medium E is positive. No change in color is negative.

Growth in the medium F is positive. Fluorescence may also be read on this medium.

The medium G is observed for good growth, poor growth or no growth.

The sensitivities on the medium H as in the Kirby-Bauer method, and susceptibility or resistance for colistin or penicillin is recorded. Any pigment produced by the organism in medium H is noted.

At this point, the information necessary for a presumptive generic identification of the organism has been obtained. This information is sufficient to characterize the genera by reference to Table I. Further subdivisions are possible when OF dextrose, as shown in Table I, is used.

TABLE I

Rapid Identification of Non-fermenting Gram Negative Organisms

| Genera | Motility | Oxidase[1] | OF Dextrose | Nitrate[2] | Pigment |
|---|---|---|---|---|---|
| Achromobacter | + | + | +[3] | +/+/− | − |
| Alcaligenes | + | + | − | +/+/− | − |
| Pseudomonas | + | +[4] | 0 0 +[5] | +/+/− | V[6] |
| Xanthomonas | +$_w$[7] | +/− | + | − | Y |
| Chromobacterium | + | − | + | 30 | Y |
| Flavobacterium | − | 30 | +/− | −/+ | Y[8] |
| Moraxella[9] | − | + | − | +/− | − |
| Acinetobacter anitratus[10] | − | − | + | − | − |
| Acinetobacter lwoffi | − | − | − | − | − |

[1] Do not do oxidase test on colonies from EMB; do not use a nichrome loop.
[2] Nitrate reduced to nitrite: +; to nitrogen gas: ++ /+/− shows the reactions by varying strains or species in the genus, in order of frequency.
[3] Do OF xylose on motile non-pigmented organisms since all Achromobacter are xylose positive but not all are dextrose positive.
[4] Ps. maltophilia usually is oxidase negative and Ps. cepacia may be.
[5] Ps. alcaligenes and Ps. diminuta are inert and resemble Alcaligenes.
[6] Pseudomonads may vary from non-pigmented through various colors of yellows, greens & reds.
[7] Xanthomonas is weakly motile, by wet mount only.
[8] Most, but not all Flavobacterium are yellow, but all are indol positive.
[9] Moraxella are diplococci resembling Neisseria; Mima polymorpha var. oxidans was actually several different Moraxella species.
[10] Acinetobacter anitratus was Herellea vaginicola; it is dextrose and lactose positive on OF media and may be blue on EMB. Ac. lwoffi was Mima polymorpha and is inert.

Having made a preliminary generic identification of the organism with the use of Table I, the medium A is observed to determine the extent of nitrate reduction which occurred. The oxidation of the specific carbohydrates comprising the media B, C and D is noted. Any reactions in the media E, F and G also are observed. The zone around the antibiotic disc on medium H is measured, and the susceptibility or resistance of the organism to the antibiotic is recorded. Reference can then be made to Table II to make a positive identification of the organism.

Table II

Identification of Nonfermentative Rods

| | Achromobacter (IIIa)** | Achromobacter (IIIb) | Achromobacter (Vd) | Alcaligenes faecalis | A. odornas | A. bronchiseptica | Pseudomonas aeruginosa | P. fluorescens | P. pudita | P. pseudomallei |
|---|---|---|---|---|---|---|---|---|---|---|
| FLAGELLA | *P | P | P | P | P | P | 1 | >1 | >1 | >1 |
| MOTILITY | + | + | + | + | + | + | + | + | + | + |
| OXIDASE | + | + | + | + | + | + | + | 30 | + | + |
| PIGMENT | − | − | − | − | − | − | G | YG | YG | Ywr |
| | | | | | | | | Fluorescent | | |
| $NO_3/N_2$ | −/+ | + | + | − | −/+ | ± | +/+ | − | − | +/+ |
| XYLOSE | + | + | + | − | − | − | + | + | + | + |
| GLUCOSE | − | − | + | − | − | − | + | + | + | + |
| LACTOSE | − | − | − | − | − | − | − | +/− | − | + |
| ESCULIN | − | − | 30 | − | − | − | − | − | − | +/− |
| CETRIMIDE | + | + | − | − | + | − | + | + | + | − |
| SS AGAR | + | + | + | +/− | + | + | + | + | + | − |
| COLISTIN | S | S | S | S | S | S | S | S | S | R |

| | P. cepacia | P. stutzeri | P. mendocino | P. putrefaciens | P. maltophilia | P. diminuta | P. alcaligenes | P. pseudoalcaligenes | Xanthomonas sp. (IIk-1/2) | Chromobacterium typhiflavum (VE-1/−2) | Flavobacterium meningosepticum (IIa) |
|---|---|---|---|---|---|---|---|---|---|---|---|
| FLAGELLA | >1 | 1 | 1 | 1 | >1 | 1 | 1 | 1 | 1 | 1/>1 | − |
| MOTILITY | + | + | + | + | + | + | + | + | +$_w$ | + | − |
| OXIDASE | + | + | + | + | − | + | + | + | +/− | 31 | + |
| PIGMENT | Y$_{sm}$ | Y$_{wr}$ | Y$_{sm}$ | (T) | T | T | − | − | Y | Y | Y$_{sc}$ |
| $NO_3/N_2$ | +/− | + | + | + | +/− | − | +/− | + | − | + | − |
| XYLOSE | + | + | + | − | ± | − | − | − | + | + | − |
| GLUCOSE | + | + | + | + | + | − | − | − | + | + | + |
| LACTOSE | + | − | + | +/− | + | − | − | − | + | − | + |
| | | | | | | | | | | +(1) | |
| ESCULIN | + | − | − | −/+ | + | − | − | − | + | −(2) | + |
| CETRIMIDE | +/− | − | −/+ | − | − | − | −/+ | + | − | − | − |
| SS AGAR | − | +/− | + | −/+ | − | − | − | −/+ | − | − | − |
| COLISTIN | R | S | S | R | S | R | S/R | S | R | S/R | R |

| | Flavobacterium sp. (saccharolytic) (IIb) | Flavobacterium sp. (proteolytic) (IIf) | Moraxella oslo-ensis | M. phenylpyruvica | M. non-liquefaciens | Acinetobacter anitratus | A. lwoffi |
|---|---|---|---|---|---|---|---|

Table II-continued

Identification of Nonfermentative Rods

| | | | | | | | | |
|---|---|---|---|---|---|---|---|---|
| FLAGELLA | − | − | − | − | − | − | − | |
| MOTILITY | − | − | − | − | − | − | − | |
| OXIDASE | + | + | + | + | + | − | − | |
| PIGMENT | Y | Y | $T_D$ | − | − | − | − | |
| $NO_3/N_2$ | −/+ | − | +/− | +/− | +/− | − | − | |
| XYLOSE | − | − | ± | − | − | + | − | |
| GLUCOSE | + | − | − | − | − | + | − | |
| LACTOSE | − | − | − | − | − | + | − | |
| ESCULIN | + | − | − | − | − | − | − | |
| CETRIMIDE | − | − | − | − | − | − | − | |
| SS AGAR | − | − | − | − | − | − | − | |
| COLISTIN | R | S | S | S | S | S | S | |

| | A. bronchiseptica | Pseudomonas aeruginosa | P. flourescens | P. putida | P. putrefaciens | P. maltophilia | P. diminuta |
|---|---|---|---|---|---|---|---|
| SPECIAL CHARACTERS | Urea + | 42° + | rhamnose + | − | D nase + $H_2S$ + | | |

| | Xanthomonas sp. (IIk-½) | Flavobacterium meningosepticum (IIa) | Flavobacterium (saccharolytic) (IIb) | Flavobacterium sp. (proteolytic) (IIf) | Moraxella osloensis | M. phenylpyruvica | M. nonliquefaciens |
|---|---|---|---|---|---|---|---|
| SPECIAL CHARACTERS | Pen. S | All Indol + | | | All Pen. S | | |

*CODE: P peritrichous; +w: weak; G: green; Y: yellow; wr: wrinkled; sm: smooth; T: tan, $NO_3/N_2$: $NO_3$ reduced to $NO_2$: +; to $N_2$: +; Colistin/Pen.: S: susceptible; R: resistant; (T): delayed pigmentation; Double lines: flagella
**Roman numerals in parentheses are CDC designations for similar organisms.

In utilizing the device to identify yeast pathogens, the media A, B, C, D, E, F and G in the wells 16 comprise nitrogen base agar containing 1%, by weight, of glucose (dextrose), maltose, sucrose, lactose, raffinose, trehalose and inositol, respectively. The medium H in the well 18 will contain Christensen's urea agar. Inoculation of the media in the device may be accomplished utilizing standard equipment and techniques. A suitable indicator such as bromthymol blue advantageously is incorporated in the media to aid in the observation of organism generated activity.

The eight media named above comprise means for the identification of the 28 yeasts listed in Tables IIIA and IIIB. Identification by means of the media in the device may be supplemented by use of additional media to provide more subtle differentiation between certain organisms. Thus, to effect separation of such yeasts as Candida parapsilosis from Candida tropicalis, a standard maltose fermentation tube may be used. Candida tropicalis ferments maltose and sucrose, while Candida parapsilosis does not ferment either sugar.

In Tables IIIA and IIIB, the plus (+) sign indicates growth (assimilation); the negative (−) sign indicates no growth. The tables also set forth other reactions of the yeasts listed. These tests are conventionally employed in the identification of yeast pathogens and supplement the information provided by the media in the device of this invention.

TABLE IIIA

| | Assimilations | | | | | | | | Other Reactions | | | | | |
|---|---|---|---|---|---|---|---|---|---|---|---|---|---|---|
| | Dextrose | Maltose | Sucrose | Lactose | Raffinose | Trhalose | Inositol | Dulcitol | Urease | $KNO_3$ | Pseudohyphae | Growth at 37C | Germ tubes | India ink capsule |
| Torulopsis glabrata | + | − | − | − | − | + | − | − | − | − | − | + | − | − |
| T. etchellsii | + | + | − | − | − | − | − | − | − | + | − | − | − | − |
| T. stellata | + | − | + | − | + | − | − | − | − | − | − | − | − | − |
| T. candida | + | + | + | +* | + | + | − | +* | − | − | − | + | − | − |
| T. inconspicua | + | − | − | − | − | − | − | − | − | − | − | + | − | − |
| Saccharomyces cerevisiae | + | + | + | − | + | +* | − | − | − | − | + | + | − | − |

| | Assimilations | | | | | | | | Other Reactions | | | | | |
|---|---|---|---|---|---|---|---|---|---|---|---|---|---|---|
| | Dextrose | Maltose | Sucrose | Lactose | Raffinose | Trehalose | Inositol | Dulcitol | Urease | $KNO_3$ | Pseudohyphae | Growth at 37C | Germ tubes | Inida ink capsule |
| Candida albicans | + | + | + | − | − | + | − | − | − | − | + | + | + | − |
| C. stellatoidea | + | + | − | − | − | +* | − | − | − | − | + | + | + | − |
| C. parapsilosis | + | + | + | − | − | + | − | − | − | − | + | + | − | − |
| C. tropicalis | + | + | + | − | − | + | − | − | − | − | + | + | − | − |
| C. pseudotropicalis | + | − | + | + | + | − | − | − | − | − | + | + | − | − |
| C. krusei | + | − | − | − | − | − | − | − | +* | − | + | + | − | − |
| C. quillermondii | + | + | + | + | − | + | − | + | − | − | + | + | − | − |
| C. rugosa | + | − | − | − | − | − | − | − | − | − | + | − | − | − |

* = strain variation, +* means usually positive, some may be negative

TABLE IIIB

| | Assimilations | | | | | | | | Other Reactions | | | | | |
|---|---|---|---|---|---|---|---|---|---|---|---|---|---|---|
| | Dex-trose | Mal-tose | Su-crose | lac-tose | Raff-inose | Tre-halose | Inos-itol | Dul-citol | Ur-ease | KNO$_3$ | Pseudo-hyphae | Growth at 37C | Germ tuber | India ink capsule |
| Cryptococcus neoformans | + | + | + | − | +* | + | + | + | + | − | R | +* | − | + |
| C. uniquttulatus | + | + | + | − | +* | +* | + | − | + | − | − | − | − | + |
| C. albidus var. albidus | + | + | + | +* | + | + | + | +* | + | + | +* | + | − | + |
| C. laurentii | + | + | + | + | +* | + | + | + | + | − | − | + | − | + |
| C. luteolus | + | + | + | − | −* | + | + | +* | + | − | − | − | − | − |
| C. albidus var. diffluens | + | + | + | − | + | + | + | +* | + | + | −* | + | − | + |
| C. terreus | + | +* | −* | −* | − | + | + | +* | + | + | −* | ° | − | + |
| C. gastricus | + | + | −* | − | − | + | + | − | + | − | −* | − | − | + |

| | Assimilations | | | | | | | | Other Reactions | | | | |
|---|---|---|---|---|---|---|---|---|---|---|---|---|---|
| | Dex-trose | Mal-tose | Su-crose | lac-tose | Raff-inose | Tre-halose | Inos-itol | Dul-citol | Ur-ease | KNO$_3$ | Pseudo-hyphae | Growth at 37C | Growth in Malt Extract broth |
| Trichosporon cutaneum | + | +* | +* | + | +* | +* | +* | +* | +* | − | + | +* | Pellicle or ring blastospores seen |
| Trichosporon pullulans | + | + | + | + | +* | + | +* | − | + | +. | + | + | Pellicle or ring with islets |
| T. penicillatum | + | − | − | − | − | − | − | − | − | − | + | + | White wrinkled pelicle |
| T. capitatum | + | − | − | − | − | − | − | − | − | − | + | + | Wrinkled pellicle, may be submerged |
| T. inkin | + | + | + | + | − | + | + | − | − | − | + | + | Pellicle found |
| Geotricum candidum | + | − | − | − | − | − | − | − | − | − | − | − | Pellicle or white islets |

* = strain variation

As stated hereinabove, the device of the present invention also can be employed as a valuable tool in the identification of microorganisms other than yeast pathogens. More specifically in this connection, the device can be used to advantage, for example, in the identification of microorganisms classified in the family Enterobacteriaceae. The pathogens in this family are highly important in the clinical laboratory because of the frequency of their occurrence in pathological specimens.

Conventional methods for identification of members of this family involve the use of media whose biochemical reactions comprised the parameters of recognition. While determinations such as urea hydrolysis, indol, hydrogen sulfide, lysine and ornithine decarboxylation, motility, citrate usage, DNase, phenylalanine deamination and fermentation of lactose, sucrose, dextrose, dulcitol, rhamnose and adonitol would suffice to characterize any species of the family, the media, and the manipulation steps required to carry out the tests, are expensive and cumbersome. However, many laboratories have continued to use many, if not all, of them in the course of identification procedures. Clearly, a series of tests numbering 15 to 20 is primarily a research project and is more attuned to a reference laboratory than a busy clinical laboratory in which speed is usually as important as accuracy, when the physician needs a rapid report to aid in diagnosis and treatment while the patient is still able to respond. Commercially available identification systems which display some of the tests named, each with its own choice of parameters, vary from tubed, multi-test media with several reactions per tube, to cups of media on cardboard strips and chemically impregnated blotting paper strips. All of these systems have advantages and shortcomings. The systems which have a fixed pattern of reactions have the advantage of having the parameters of identification chosen by bona fide experts and with keys accompanying them to facilitate identification. The less carefully controlled systems which can be set up in a mix-and-match sequence offer flexibility, but provide no guidance to the technologist, and, thus, are effective only to the extent of his knowledge of identification parameters.

The device of the present invention affords the technician of average ability greater than average or even near expert skill in the identification of the Enterobacteriaceae group. The media used include some which are not found in any of the existing systems, and serve to facilitate identification of species which are presently impossible to differentiate with any of the existing systems. The media used in the device for this purpose are as follows:

An indicator such as bromcresol purple is incorporated in the media in each instance where the activity of the organism under investigation can be elicited by a color change in the media.

Well A — Tryptophane deaminase-urea-indol agar. This medium offers three separate biochemical reactions: (1) deamination of tryptophane, (2) production of indol from tryptophane, and (3) urea hydrolysis.

Well B — ONPG. A more sensitive test than lactose fermentation, ortho-nitrophenyl-beta-galactopyranoside (ONPG) detects beta-galactosidase quickly, so that late lactose fermenters are rapidly identified by production of yellow color.

Well C — Dextrose-H$_2$S. The high protein-to-carbohydrate ratio prevents dextrose assimilation by non-fermentative rods and a change of the bromcresol purple indicator in the medium from purple to yellow denotes the production of acid from dextrose and a positive reaction. A failure to ferment dextrose would indicate that the organism is not a member of Enterobacteriaceae. The detection of H$_2$S gas results from the production of blackening of the medium along the stab lines by the formation of ferrous sulfide.

Well D — Lysine decarboxylase. Anaerobic decarboxylation of lysine is shown by the color change of the pH indicator bromcresol purple in the medium from straw color to deep purple (positive).

Well E — Ornithine decarboxylase. Ornithine reacts similar to lysine. Both reactions are carried out under sealants such as paraffin, cellophane or plastic well covers to reduce the oxidation of the medium. Decarboxylation is an anaerobic reaction.

Well F — Simmon's citrate. The ability to utilize citrate as a carbon source in the presence of an inorganic salt of nitrogen is a test of the synthetic ability of microorganisms and an identification parameter.

Well G — Christensen's citrate. Citrate utilized in the presence of amino acid nitrogen is more common, but Shigella, an important pathogen causing dysentery, stands almost totally alone in its inability to use citrate with either nitrogen source.

Well H — DNase/arabinose. The predisposition of the enzyme DNase to attack deoxyribonucleic acid is characteristic of the genus Serratia and the formation of a clear zone with a pink border around the streaked colony, replacing the blue color of the original agar constitutes a positive and a presumptive identification. The fermentation of arabinose is a differential parameter separating Aeromonas, non Enterobacteriaceae, which are also DNase positive from Serratia. Although Aeromonas should have been detected by the oxidase test prior to inoculation of the Well H, invariably some will be placed on the media in the device because they appear to be enteric and Well H will reveal the error.

Table IV indicates the salient parameters which rapidly delineate organisms within the family Enterobacteriaceae, as shown by Proteus, so that the technician can obtain the guidance to enable an accurate identification to be made. The plus (+) sign is employed in the table to indicate a positive reaction, while the minus (−) sign represents a negative reaction.

blood agar plates and place them in anaerobic jars. Identification is almost non-existent even at this level with merely the shape, Gram reaction and spores mentioned if seen.

The device of this invention provides an excellent vehicle for enabling laboratory personnel of even average capabilities to accurately identify the most commonly encountered anaerobic pathogens. The media used for this purpose is as follows:

Well A — Dextrose agar containing bromthymol blue as an indicator. The agar is blue when inoculated. Fermentation or assimilation of the dextrose produces a yellow color.

Well B — Xylose agar containing the same indicator, and manifesting the same change in color.

Well C — Maltose agar containing bromthymol blue. A positive reaction is manifested as in the case of Wells A and B.

Well D — Rhamnose agar containing bromthymol blue. A positive reaction is manifested as described above for Well A.

Well E — Trehalose agar containing bromthymol blue. Activity or non-activity is manifested as in the case of Well A.

Well F — Indol nitrite agar. Indol is extracted with xylene after the cover has been removed for 30 minutes, and tested with Kovac's solution. Development of a red color is positive; a yellow color is negative.

Well G — Esculin. Development of a brown color, or the loss of fluorescence under 3660 A black light rays is a positive reaction.

Well H — 2% bile agar. Inhibits the growth of many organisms. Growth is positive, and for some organisms, growth is enhanced.

The device, with the media, and after inoculation, is incubated in an anaerobic jar made oxygen-free by any of three conventional methods: (a) "gassing-out" of the jar with flowing nitrogen-hydrogen-carbon dioxide gas mix, (b) use of a gas-pack commercial unit, or (c) glove box anaerobic atmosphere for filling the jar and maintaining the media under oxygen-free conditions. When incubated for a 48 hr. minimum period, the reactions of the culture can be read and compared with Table V for the proper identification of the organism. The plus (+) and minus (−) signs are used in Table V to represent positive and negative activity, respectively.

TABLE IV

|  | Tryptophane deam. | Urea | Indol | H$_2$S | ONPG | Dextrose | Lysin | Ornithine | Simmon's Citrate | Christensen' Citr. | DNase | Arabinose |
|---|---|---|---|---|---|---|---|---|---|---|---|---|
| (Genus) Providencia | + | − | + | − | − | + |  |  |  |  |  |  |
| (Genus) Proteus | + | + |  |  |  |  |  | + |  |  |  |  |
| Proteus mirabilis |  |  |  | + |  |  |  | − |  |  |  |  |
| " vulgaris |  |  |  | + |  |  |  | + |  |  |  |  |
| " morganii |  |  |  | − |  |  |  | + |  |  |  |  |
| " rettgeri |  |  |  | − |  |  |  |  |  |  |  |  |
| (Genus) Yersinia | − | + |  |  |  |  |  |  |  |  |  |  |
| " Escherichia | − | − | + | − | − |  | ± |  | − | + |  |  |
| " Shigella |  |  | ± | − | ± |  | − |  |  |  |  |  |
| " Edwardsiella |  |  | + | + | − |  | + |  |  |  |  |  |
| " Salmonella |  |  | − | + | − |  | + |  |  |  |  |  |
| " Arizona |  |  | − | + | + |  | + |  |  |  |  |  |
| " Citrobacter |  |  | − | ± | ± |  | − |  | + |  |  |  |
| " Klebsiella |  |  | − | − | + |  | + | − |  |  | − |  |
| " Enterobacter |  |  |  |  |  |  | ± | ± |  |  | + | − |
| " Serratia |  |  |  |  |  |  | + | + |  |  | + | + |
| " Aeromonas) |  |  |  |  |  |  |  |  |  |  |  |  |

The use of the device for the identification of anaerobes has been mentioned hereinabove. Up to now many laboratories have limited their involvement with pathogenic anaerobes to simply placing specimens in thioglycollate broth, and reporting as anaerobes any organisms seen on smears from cultures that were not seen on aerobically incubated plates from the same specimen. Others, more sophisticated, streak anaerobic

TABLE V

Differential Characteristics of Anaerobes* Commonly Isolated from Clinical Specimens

| | Dextrose | Maltose | Xylose | Rhamnose | Trehalose | Indol | Esculin | 2% bile | |
|---|---|---|---|---|---|---|---|---|---|
| GRAM NEGATIVE RODS | | | | | | | | | |
| Bacteriodes | | | | | | | | | |
| B. Clostridiiformis | + | + | + | | | — | —+ | | motile |
| B. fragilis ssp ovatus | + | + | + | + | + | + | + | + | mann. + |
| " thetaiotaomicron | + | + | + | + | + | + | + | + | = — |
| " distasonis | + | + | + | + | + | — | + | + | |
| " vulgatus | + | + | + | ± | — | — | +⁻ | + | |
| " fragilis | + | + | + | — | — | — | + | + | |
| B. oralis | + | + | — | — | — | — | +ᵥᵥ | — | |
| B. melaninogenicus | | | | | | | | | black colonies on blood |
| ssp intermedius | + | ± | — | — | — | ± | — | + | agar, red |
| " assacharolyticus | — | — | — | — | — | ± | — | + | fluorescence |
| B. corrodens | — | — | — | — | — | — | — | — | pitted on blood agar |
| Fusobacterium mortiferum | + | + | — | — | — | — | +⁻ | + | |
| F. necrophorum | + | +⁻ | — | — | — | + | — | — | |
| F. nucleatum | + | — | — | — | — | + | — | | |
| GRAM POSITIVE RODS* | | | | | | | | | |
| Actinomyces israelii | + | + | +⁻ | — | ± | — | +⁻ | | |
| A. naeslundii + | +⁻ | — | — | + | — | +⁻ | facultative | | |
| A. odontolyticus | + | + | ± | + | + | — | ± | | urea positive |
| Bifidobacterium eriksonii | + | + | + | — | ± | — | +⁻ | | |
| Eubacterium alactolyticum | + | — | — | — | — | — | — | | |
| E. lentum | — | — | — | — | — | — | — | | |
| E. limosum | + | — | — | — | — | — | ± | | |
| Proprionibacterium acnes | + | — | — | — | — | +⁻ | — | | |
| P. granulosum | + | + | — | — | + | — | — | | |
| GRAM POSITIVE COCCI | | | | | | | | | |
| Peptococcus saccharolyticus | + | — | — | — | — | — | — | | |
| P. asacharolyticus | — | — | — | — | — | + | — | | |
| Peptostreptococcus | | | | | | | | | |
| anaerobius | + | +⁻ | — | — | — | — | — | | |
| P. intermedius | + | + | ± | — | ± | — | + | | |

*not including the genus Clostridium, sporeforming rods. Code: ± =variable; +⁻= mostly +, few —; w = weak reactions.

While the invention has been described and illustrated with reference to a preferred embodiment, the invention is not intended to be limited to the precise construction disclosed, it being understood that various modifications, including changing the shape of the device, varying the number of wells and the type of media employed, may be suggested to those having the benefit of the teachings herein without departing from the scope of the invention.

What is claimed is:

1. A device for use in the identification of microorganisms, comprising: a microorganism culture medium receiving portion having a plurality of culture medium receiving compartments formed therein, and a cover for the culture medium receiving portion having a top wall and a depending side wall, said culture medium receiving portion having an outer, upwardly extending side wall the upper margin of which engages and maintains the top wall of the cover in spaced apart relation to the upper surface of a microorganism culture medium contained in the compartments of the culture medium receiving portion, said culture medium receiving portion side wall having a section which extends inwardly along the horizontal plane of the culture medium receiving portion toward the center thereof to provide a culture medium orienting recess in the culture medium receiving portion between at least two of the compartments formed therein, said inwardly extending section of the side wall being of reduced height in relation to the remainder of the side wall along its inward extension toward the center of the culture medium receiving portion to provide, in cooperation with the cover, a covered air-passageway at said recess in communication with the space between the upper surface of the compartments formed in the culture medium receiving portion and the top wall of the cover for enabling an atmosphere which favors the growth of microorganisms to be selectively established over the culture medium in the compartments of the culture medium receiving portion while the culture medium is shielded from culture medium contaminants by the cover.

2. A device according to claim 1 wherein the compartments are arranged in substantially circular relation to one another, and the recess is formed adjacent to the point of separation of at least two of the compartments.

3. A device according to claim 1 wherein the culture medium receiving portion comprises eight wells integrally formed therein, one of the wells being substantially centrally and concentrically positioned with relation to the remaining seven wells and adjacent to the innermost end of the recess.

4. A device according to claim 3 wherein each of the wells contains a different microorganism culture medium, each medium being characterized in that it will elicit indicia in response to microorganism activity which can be correlated with indicia elicited by each of the other media to provide sufficient indicia for the accurate identification of a microorganism under investigation.

5. A device according to claim 4 wherein the media comprise a solid culture medium base, the base in each well containing at least one of the following: glucose, maltose, sucrose, lactose, raffinose, trehalose, inositol or Christensen's urea agar, said media being capable of eliciting indicia of activity by a yeast pathogen.

6. A device according to claim 4 wherein the medium in each of the wells contains at least one of the following: tryptophane deaminase-urea-indol agar, ortho-nitrophenyl-beta-galactopyranoside, dextrose, lysine carboxylase, ornithine decarboxylase, Simmon's citrate, Christensen's citrate, or a mixture of deoxyribonuclease and arabinose, said media being capable of eliciting indicia of activity by microorganisms of the family Enterobacteriaceae.

7. A device according to claim 4 wherein the medium in each of the wells contains at least one of the following: dextrose, xylose, maltose, rhamnose, trehalose, indol, esculin or bile, said media being capable of eliciting indicia of activity by anaerobic microorganisms.

8. A device according to claim 4 wherein the media comprise a solid culture medium base, the base in each well containing at least one of the following: Seller's medium, xylose, glucose, lactose, esculin agar, cetrimide agar, SS agar, and Mueller-Hinton medium, said media being capable of eliciting indicia of activity by a non-fermentative Gram negative rod.

* * * * *